United States Patent [19]  
Hill

[11] 4,086,488  
[45] Apr. 25, 1978

[54] DIGITAL PRESSURE GAUGE SYSTEM
[75] Inventor: James J. Hill, North Miami, Fla.
[73] Assignee: General Medical Appliance Research Corporation, Miami, Fla.
[21] Appl. No.: 733,284
[22] Filed: Oct. 18, 1976
[51] Int. Cl.² ............................................. G01D 5/34
[52] U.S. Cl. .......................... 250/231 P; 250/231 SE
[58] Field of Search ......... 250/231 R, 231 SE, 237 R, 250/237 G, 231 P; 324/175; 356/169, 170; 340/347 P

[56] References Cited  
U.S. PATENT DOCUMENTS

| 3,237,012 | 2/1966 | Treffeisen | 250/231 P |
| 3,818,224 | 6/1974 | Schmidt | 250/237 R |
| 3,916,185 | 10/1975 | Jehly | 250/231 SE |
| 3,999,064 | 12/1976 | Kramer | 340/347 P |

Primary Examiner—David C. Nelms  
Attorney, Agent, or Firm—Oltman and Flynn

[57] ABSTRACT

The digital pressure gauge system is particularly useful for reading blood pressures of humans, and has general utility in dial or disc type gauges for reading liquid and gas pressures. The digital pressure gauge system includes a rotary encoder which takes the place of the dial or disc of a conventional pressure gauge and therefore rotates to a degree proportional to the magnitude of the pressure being read. The rotary encoder carries a plurality of light sources which are selectively located for encoding particular angular positions of the rotary encoder. These light sources selectively direct light on photosensors which are connected by circuitry to digital readouts for converting the encoded information into a digital display. The displays may be contained in the gauge unit or they may be located remotely from the gauge unit if desired.

9 Claims, 7 Drawing Figures

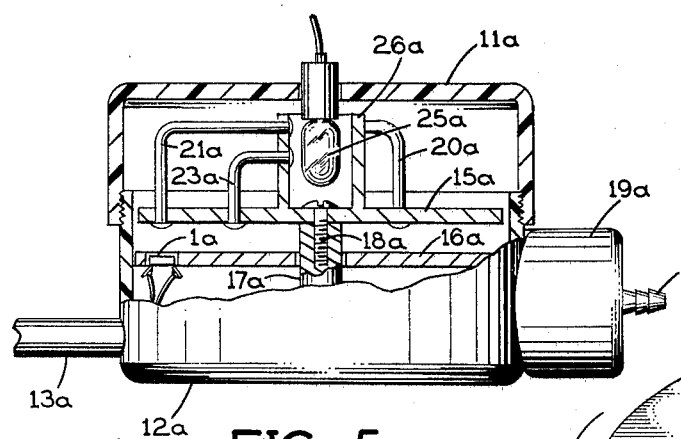
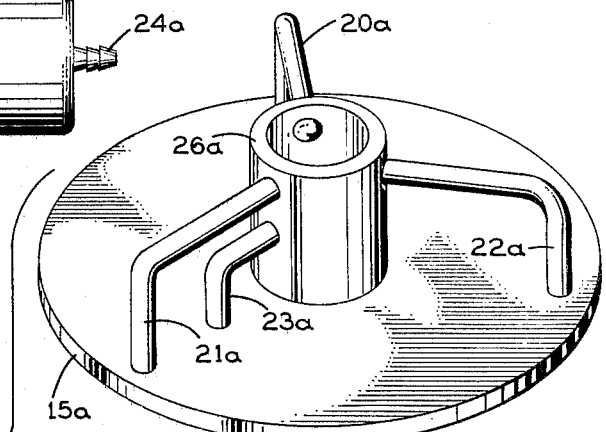
FIG. 5
FIG. 6
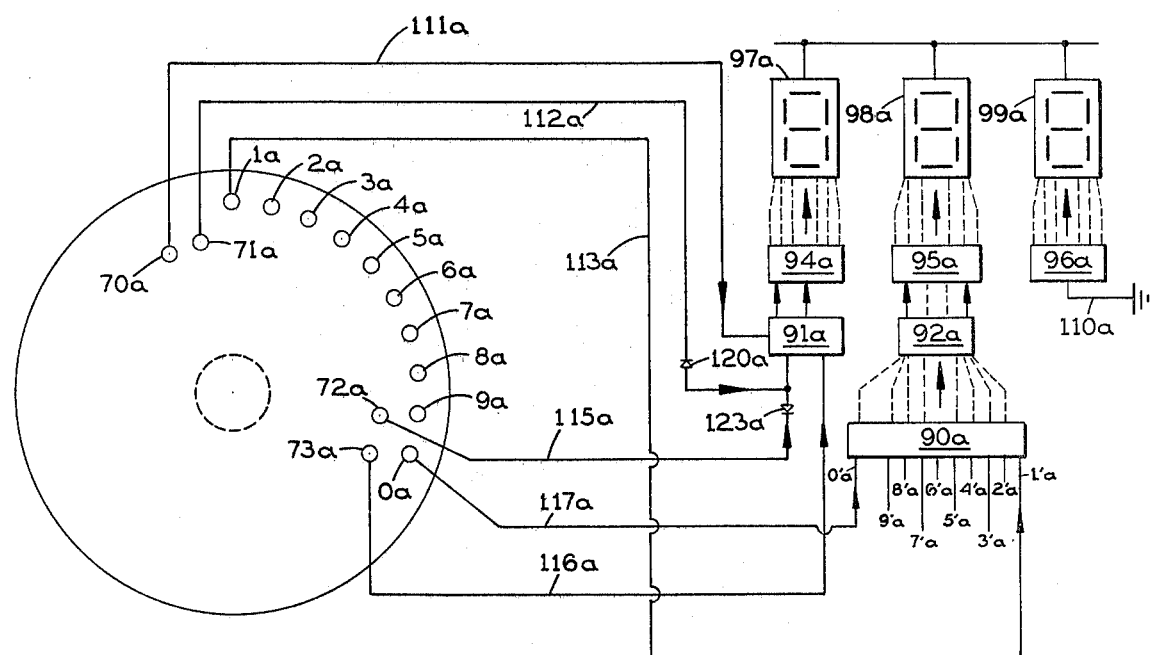
FIG. 7

DIGITAL PRESSURE GAUGE SYSTEM

BACKGROUND OF THE INVENTION

Some conventional gas and liquid pressure gauges have a dial or disc type graduated display for reading of pressure values. It is difficult to read such gauges at any distance, and inaccuracies in readings are not uncommon, particularly when unskilled personnel are using the gauge. Blood pressure gauges are finding greatly increased usage as increased effort and education is being put into encouraging people to have their blood pressure taken.

SUMMARY OF THE INVENTION

The present invention is a digital gauge system having easy to read digital displays which may be located within the gauge unit itself or at a remote location from the actual gauge unit. The displays obtain their readout accuracy directly from a rotating element of the gauge mechanism without requiring any restriction or resistance which would tend to alter the accuracy of the gauge. The gauge includes a rotary encoder, preferably in the form of a rotor disc, which carries a plurality of light sources having predetermined locations for encoding selected angular positions of the rotor disc. These light sources direct light onto photosensors, preferably phototransistors, which feed information through logic circuitry to the digital displays which display the numerical readout. Thus, a true gauge reading is obtained which is much easier to read either visually at the gauge, or at a remote location if the displays are located remotely, than a dial or disc type of graduated readout.

An object of the present invention is to provide an accurate, direct reading gauge having a digital readout display.

A further object of this invention is to eliminate any need for pressure transducers in a digital pressure gauge system.

Another object of the invention is to provide an accurate gauge with digital readouts using numerical, easy to read, gaseous or light-emitting diode type displays, which may be located at the gauge itself or remotely located, if desired, and which obtain their readout accuracy directly from the rotating element of the gauge mechanism without the addition of any rotation restriction or resistance which would tend to alter the accuracy of the gauge.

Another object of the invention is to employ selectively positioned light sources on a rotary encoder cooperating with stationary photosensors for encoding the angular position of the rotary element of the gauge mechanism.

A further object of the invention is to convert electrical information supplied from the foregoing photosensors into numerical form utilizing logic circuitry.

Further objects and advantages of this invention will be apparent from the following detailed description of a presently-preferred embodiment thereof, which is shown in the accompanying drawings.

BRIEF DESCRIPTION OF THE DRAWINGS

FIG. 5 is an elevational view, partly in section, of a gauge body forming another embodiment of the invention;

FIG. 6 is an exploded perspective view showing a rotary encoder disc and a stationary circuit board carrying photosensors in accorance with the embodiment of FIG. 5; and FIG. 7 is a schematic diagram of the electrical circuitry for the embodiment of FIGS. 5 and 6.

Figure 1:
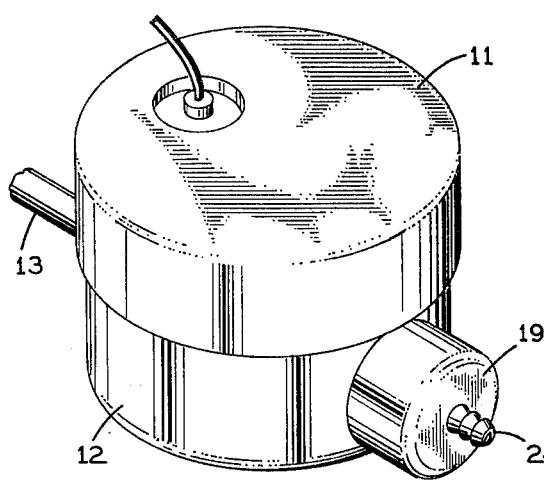
FIG. 1 is a perspective view of a gauge body modified to provide digital readouts in accordance with a preferred embodiment of the invention.

Before explaining the disclosed embodiments of the present invention in detail, it is to be understood that the invention is not limited in its application to the details of the particular arrangements shown, since the invention is capable of other embodiments. Also, the terminology used herein is for the purpose of description and not of limitation.

DETAILED DESCRIPTION

Referring first to FIGS. 1-4, the gauge body 12 and cover 11 are conventional components of a standard pressure gauge utilizing a conventional gauge mechanism having a rotary shaft 17 which rotates to a degree proportional to the magnitude of gas pressure supplied to a gas pressure inlet 24. The mechanism of the gauge body is not illustrated herein since it may be conventional so long as it rotates the shaft 17 proportional to the magnitude of the gas pressure being monitored. The gas pressure of the particular unit to be described herein is the gas pressure of a blood pressure testing unit. Part of the mechanism of the gauge body is contained in the housing extension 19. Wiring for the electrical circuitry of the digital display system of the invention extends through a cable 13 to a digital display which includes three display units 97, 98 and 99 shown in FIG. 4. The display units may be associated directly with the gauge body 11, 12 or they may be located remotely from the gauge body if desired.

Figure 3:
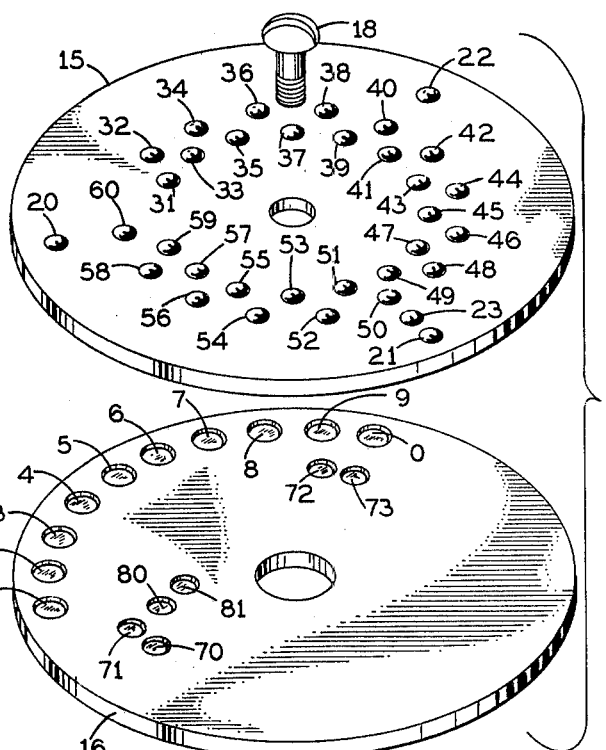
FIG. 3 is an exploded perspective view showing a rotary encoder disc and a stationary circuit board carrying photosensors which cooperate to encode the angular position of the rotary shaft of the gauge mechanism illustrated in FIG. 2.

Located within the gauge 11, 12 is a rotary encoder disc 15 which is attached to the rotary shaft 17 as with a screw 18. Just below the rotary encoder disc 15, there is a stationary circuit board (stator board) 16. The rotary encoder disc 15 carries a plurality of light sources 20-23 and 31-60 as shown in FIG. 3. These light sources may be fiber optic lenses which receive light from a bulb 25 having a reflector 14 attached to the cover 11 of the gauge. The stationary circuit board 16 carries photosensors which are preferably phototransistors 1-0, 70-73, and 80-81. The photosensors may be mounted in corresponding openings in the board 16, either under the board or on top of the board. The wiring from the photosensors extends through the cable 13 to the display units 97, 98 and 99 as previously mentioned.

The rotary encoder 15 and the stator board 16 may be added to a conventional gauge body with a conventional gauge mechanism. The rotary encoder 15 replaces the arrow or needle of the gauge body and the stator board 16 is mounted under the rotary encoder as shown in FIG. 2.

Figure 2:
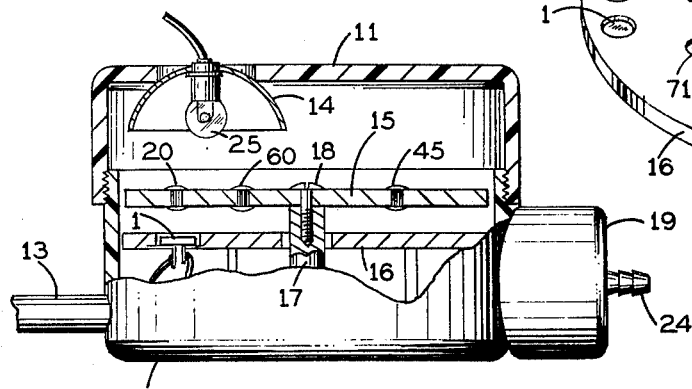
FIG. 2 is an elevational view, partly in section, of the gauge body of FIG. 1.

The section in FIG. 2 is taken when lens 20 is over sensor 1, and the section in FIG. 5 is taken when lens 21a is over sensor 1a. FIGS. 3 and 6 shown the discs in a rest position.

Sufficient light to activate a particular photosensor of the stator board 16 will pass through a lens of the rotary encoder 15 only when the particular lens in question is directly under the lamp reflector 14. Lenses 20-22 are radially aligned with sensors 1-0. Lens 23 is radially aligned with sensors 70-73. Lenses 31-60 are alternately radially aligned with sensors 80 and 81 respectively. The rotary encoder rotates clockwise as viewed from the top. The three lenses 20, 21 and 22 are spaced about 120 degrees from each other about the periphery of the rotary encoder disc 15. The lenses 20-22 serve the purpose of encoding information for providing the second significant digit of the readout display; that, is, the display unit 98. The lens 23 is located radially inward from lens 21 and provides coded information for the first significant digit of the readout display, that is, display unit 97. The display unit 99 displays numbers 0 and 5 alternately when the unit is in operation in this particular embodiment. The display unit 98 displays numerals 1-0 sequentially, and the display unit 97 displays numerals 1 and 2 sequentially as the rotary encoder disc rotates through about 320 degrees. A rotation of 320 degrees is sufficient for blood pressure testing purposes.

The photosensors 1-0 on stator board 16 cooperate with the lenses 20-22 to provide the second significant digit on the display unit 98. These photosensors are spaced at about 10 degree intervals. The photosensors 70, 71, 72 and 73 cooperate with the lens 23 to provide the first significant digit on the display unit 97. The photosensors 80 and 81 cooperate with the lenses 31-60 inclusive to provide the third significant digit on the display unit 99.

Figure 4:
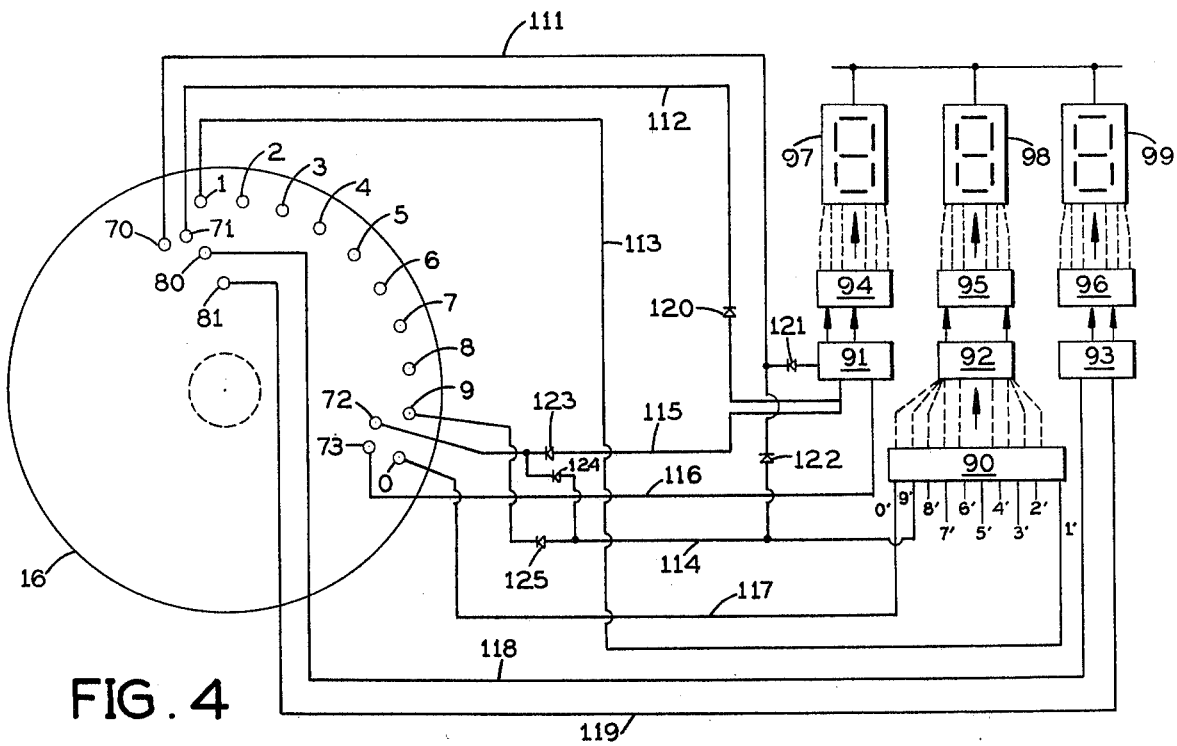
FIG. 4 is a schematic diagram of the electrical system of the digital gauge system of FIGS. 1-3.

The electrical circuit of FIG. 4 includes an up-and-down decade static switch unit 90 having ten inputs 1'-0'. Signals are sent from the unit 90 to a diode matrix 92 which in turn operates a 7 segment integrated circuit 95 for operating the 7 individual segments of the display unit 98.

A triple static switch unit 91 is connected through a diode matrix 94 to the display unit 97. A double static switch unit 93 connects through a diode matrix 96 to the display unit 99. The 7 segment integrated circuit 95 converts binary coded decimal information into 7 segment displays. The static switches 90, 91 and 93 are conventional as are the diode matrixes 92, 94 and 96.

Lines 111 and 112 connect phototransistors 70 and 71 respectively to the static switches 90 and 91. Line 113 connects phototransistor 1 to the 1' static switch input of the static switch 90. Line 114 connects the phototransistor 9 to the 9' input of the static switch 90. Line 117 connects the 0 transistor to the 0' input of the static switch unit 90. Lines 118 and 119 connect the phototransistors 80 and 81 to the double static switch 93. Lines 115 and 116 connect the phototransistors 72 and 73 to the triple static switch unit 91.

The diodes 120-125 inclusive provide proper routing of signals.

As lens 20 of the rotary encoder disc 15 passes over phototransistor 1 of stator board 16, light from lamp 25 of FIG. 1 turns phototransistor 1 on. This places voltage on lead 113 which turns on and latches static switch 1' of static switch unit 90. The output voltage from static switch 1' of static switch unit 90 connects voltage to the digit 1 diode combination of diode matrix 92, which selects the proper a, b, c, d inputs of the binary coded decimal to 7 segment integrated circuit 95. This connects voltage to the proper segments of digital display unit 98 illuminating the numeral 1. By similar circuitry the numerals 2-0 are displayed on the display unit 98 as lens 20 rotates past phototransistors 2-0 allowing those transistors to be turned on sequentially.

The outputs of the 10 individual static switches 1'-0' of the static switch unit 90 are capacity coupled so that as static switch 2' of switch unit 90 is turned on, static switch 1' is turned off. Turning on static switch 3' turns off static switch 2', and so on.

When rotary encoder disc 15 rotates to a position wherein lens 20 turns on phototransistor 0 on the stator board 16 all other phototransistors 1-9 of stator board 16 have sequentially been turned on and off registering digital display readout numerals on display unit 98 from 1 through 0.

As rotary encoder disc 15 continues to rotate, light lens 20 passes beyond the bank of 10 phototransistors 1-0, and light lens 21 approaches and passes over phototransistors 1-0 again, thus for the second time sequentially illuminating the numerals 1-0 on digital display unit 98.

As rotary encoder disc 15 continues to rotate, light lens 21 passes beyond the bank of 10 phototransistors 1-0, and light lens 22 approaches and passes over phototransistors 1-0, again for the third time sequentially illuminating the numerals 1-0 on the display unit 98. For most gauges 320 degrees of shaft rotation is the normal maximum extent of rotation.

The positions of the phototransistors 1-0 on the stator board 16 and the corresponding lenses 20-22 on the rotary encoder disc may be selected to match the calibrated locations for the gauge to be used. In this particular gauge illustration, the rotation matches gauge calibration in steps of five units, and a total rotation of 295 units.

When rotary encoder disc 15 has rotated to the position wherein lens 20 has turned on phototransistor 0 of the stator board 16, lens 23 is over phototransistor 71. This turns on phototransistor 71 and applies a voltage to lead 112 which latches in the numeral 1 section of the triple switch 91. The now latched in and turned on numeral 1 section of the triple static switch 91 supplies a signal to a diode matrix 94 which causes the numeral 1 to be illuminated on the display unit 97. The total reading on all three display units at this time would be 100.

The rotary encoder disc 15 continues to rotate until the lens 21 is over the phototransistor 0 of the stator board 16, and the numeral 0 of display unit 98 is illuminated. At this position, lens 23 is over phototransistor 73 of the stator board 16, turning on transistor 73 and applying a voltage to lead 116 which turns on and latches in the numeral 2 section and turns off the numeral 1 section of the triple static switch 91. The now latched in and turned on numeral 2 section of the triple static switch 91 supplies an output through the diode matrix 94 which illuminates the numeral 2 of display unit 97. The total reading on the three display units 97, 98 and 99 is 200 at this time.

Lead 114 from phototransistor 9 and lead 117 from phototransistor 0 illustrates that a plurality of similar circuitry is provided for phototransistors 1-0 inclusive.

When rotary encoder disc 15 has rotated to the position where lens 23 is over phototransistor 70, phototransistor 70 is turned on and voltage is applied to the lead 111 which turns on and latches in the 1 numeral off section of the triple static switch unit 91. This circuit operates only if the numeral 1 section of the triple static switch 91 has first been turned on. This same phototransistor lead 111 connects through a diode to the numeral 9' input of the decade static switch unit 90, illuminating numeral 9 of digital readout display unit 98.

Phototransistor 70 of stator plate 16 performs a double function. It also turns off the numeral 1 of the digital display unit 97 and turns on the numeral 9 of the digital display unit 98.

When the rotary encoder disc 15 rotates to a position wherein the lens 23 is over the phototransistor 72 of the stator plate 16, phototransistor 72 is turned on and voltage is applied to lead 115 which turns on and latches in the numeral 1 section of the triple static switch unit 91. This in turn applies voltage to the diode matrix 94 which illuminates the numeral 1 section of display unit 97.

Phototransistor 72 performs a triple duty function. It also turns off numeral 2 of the display unit 97 if the numeral 2 has previously been illuminated by phototransistor 73. Also, it turns on numeral 9 of display unit 98.

The rotary encoder disc 15 contains thirty lenses 31-60. The even numbered lenses in this series pass over a phototransistor 80 which applies a voltage over line 118 to a double static switch unit 93 which works diode circuitry 96 to illuminate the numeral 5 of the display unit 99. The odd numbered lenses in this series pass over a phototransistor 81 which applies a voltage over line 119 to the double static switch 93 which works through diode circuitry 96 to illuminate the numeral 0 of the display unit 99. Double static switch 93 changes back and forth between the numeral 0 and the numeral 5. This circuit enables the digital readout display unit 99 to alternately register the numeral 0 and the numeral 5 for the last significant digit of the display. Without this system, 30 phototransistors would be required to accomplish the alternation of 0's and 5's in a digital readout of three decade logic.

When the rotary encoder disc 15 has rotated to a position wherein lens 56 is over the phototransistor 80, phototransistor is turned on and voltage is applied to lead 118 which latches in and turns on the numeral 5 section of the double static switch 93. This supplies voltage to the diode matrix 96 which causes the numeral 5 to be illuminated on the display unit 99. If the numeral 0 had been illuminated previously, it will now be turned off.

When the rotary encoder disc 15 has rotated to a position whereby lens 55 is over phototransistor 81, phototransistor 81 is turned on and applies voltage to line 119 which latches in and turns on the numeral 0 section of the double static switch 93. This supplies voltage to the diode matrix 96 which causes the numeral 0 to be illuminated on the display unit 99. Since double static switch 93 is of the flip-flop type, numeral 5 will be turned off it it had been in the on condition.

The above circuit design and mechanical design economically converts gauges of the mechanical dial and scale type to the electronic digital readout type. As an example, dial readings may be in steps of five from 0 through 300. By connecting a safety pressure switch, flow switch, temperature switch or the like, in series with the lamp 25, the lamp 25 will be extinguished in the event of a system failure. Since the lamp 25 has been turned off, the digit display will remain on even though the pressure is removed.

With this system it is possible to obtain gauge readings in 60 accurate up and down steps utilizing only 16 phototransistors and one light source.

In the alternate embodiment illustrated in FIGS. 5-7, the same reference numerals are used for like elements in FIGS. 1-4 with the suffix "a" added in order to distinguish the two embodiments from each other. Only the differences in FIGS. 5-7 as compared to FIGS. 1-4 will be described. In FIGS. 5-7, the lamp 25 is located at the center of the gauge unit, and there are fiber optic arms which turn down and project through the rotary encoding disc 15a to provide the lenses. Note that there are no lenses corresponding to the lenses 31-60 in FIG. 3. Thus, the third significant digit of the readout display remains the same for all readings. The diode matrix 96a is grounded at 110a illustrating this fact. The fiber optic arms 20a, 21a, 22a and 23a correspond to lenses 20, 21 22 and 23 in FIG. 3 and the description of how these lenses function in cooperation with phototransistors 1a-0a and phototransistors 70a-73a will not be repeated. The dial readings for this embodiment is in steps of 10's. Note that lamp 25a is within a hub 26a through which the inner ends of the optic arms 20a-23a project.

Having thus described my invention, I claim:

1. In a pressure gauge system comprising pressure gauge having:
   a gauge body with a gas pressure inlet;
   a cover on said gauge body;
   a rotary shaft in said gauge body extending at one end toward said cover;
   and pressure responsive means in said gauge body for rotating said shaft proportional to the gas pressure at said inlet; the improvement which comprises:
   an encoder disc fastened to the shaft at said end and extending substantially perpendicular thereto, said disc carrying a plurality of discrete light transmitting elements at different positions radially and circumferentially of the disc;
   a lamp positioned inside said cover on the opposite side of said disc from said shaft and operatively arranged to shine light through at least one of said light transmitting elements on the disc;
   a stator plate fixedly mounted inside said gauge body on the opposite side of said disc from said lamp, said stator plate extending substantially parallel to said disc and passing said shaft rotatably;
   a plurality of photosensors mounted on said stator plate for selective registration individually with corresponding light transmitting elements on the disc in different rotational positions of the disc;
   numerical display means for displaying a three digit decimal number;
   and circuit means operatively connected between said photosensors and said numerical display means for converting the optically sensed rotational position of the shaft into the two most significant digits of the displayed three digit number.

2. A pressure gauge system according to claim 1, wherein said light transmitting elements are fiber optic lenses at said different positions on the disc, and further comprising a reflector operatively associated with said lamp to substantially concentrate the light from the lamp on a small area of the disc to illuminate just the lens or lenses which appear in said small area in different rotational positions of the disc.

3. A pressure gauge system according to claim 1, wherein said light transmitting elements are separate fiber optic arms extending individually from said lamp to said different positions on the disc.

4. A pressure gauge system according to claim 1, wherein:
said photosensors on the stator plate include an outer row of ten photosensors at the same radial distance from the shaft and evenly spaced in close succession circumferentially;
said light transmitting elements on the disc include three elements at said same radial distance from the shaft which are spaced apart circumferentially by ten times the spacing between successive ones of said ten photosensors;
said circuit means includes means connected between said ten photosensors and said numerical display means for actuating the latter to display as the second most significant digit of the three digit number ten successive digits from "1" to "0" in successive rotational positions of the shaft in the forward direction as any of said three light transmitting elements registers in succession individually with the ten photosensors;
said light transmitting elements on the disc also include a single element at a shorter radial distance from the shaft than said three light transmitting elements;
said photosensors include an inner row of first, second, third and fourth photosensors in succession circumferentially at said shorter radial distance from the shaft, said first and second photosensors in said inner row being spaced circumferentially from each other by less than the angle between successive photosensors in said outer row, said second and third photosensors in said inner row being spaced circumferentially from each other by substantially the same angular distance as the spacing between the first and tenth photosensors in said outer row, and said third and fourth photosensors in said inner row being spaced circumferentially from each other by less than the angle between successive photosensors in said outer row;
said circuit means includes means connected between said first photosensor of said inner row and said numerical display means to actuate the latter
  (a) to display the digit "9" as said second most significant digit of the three digit number, and
  (b) to prevent the display of the digit "1" as the most significant digit of the three digit number when said single light transmitting element on the disc registers with said first photosensor of said inner row;
said circuit means includes means connected between said second photosensor of said inner row and said numerical display means to actuate the latter to display the digit "1" as the most significant digit of said three digit number when said single light transmitting element on the disc registers with said second photosensor of said inner row and to maintain said display of the digit "1" as the most significant digit until said single light transmitting element registers with the fourth photosensor in said inner row, during the forward rotation of the shaft;
said circuit means includes means connected between said third photosensor of said inner row and said numerical display means to actuate the latter
  (a) to display the digit "1" as the most significant digit of said three digit numer, and
  (b) to prevent the display of the digit "2" as the most significant digit of said three digit number, and
  (c) to display the digit "9" as the second most significant digit of said three digit number when said single light transmitting element on the disc registers with said third photosensor of said inner row;
and said circuit means includes means connected between said fourth photosensor of said inner row and said numerical display means to actuate the latter
  (a) to display the digit "2" as the most significant digit of said three digit number, and
  (b) to prevent the display of the digit "1" as the most significant digit of said three digit number after said single light transmitting element on the disc registers with said fourth photosensor of said inner row during the forward rotation of the shaft.

5. A system according to claim 4 wherein:
said numerical display means includes means for displaying an "0" or a "5" as the least significant digit of the three digit number;
said light transmitting elements on the disc include rows of fifteen elements each at different radial distances from the shaft;
said photosensors on the stator plate include two photosensors positioned respectively at said last-mentioned radial distances from the shaft for registration alternately with the successive light transmitting elements in said last-mentioned two circular rows as the shaft rotates in the forward direction;
and said circuit means includes means connected between one of said last-mentioned two photosensors and said numerical display means for actuating the latter to display a "0" as the least significant digit of said three digit number when said one photosensor is activated, and means connected between the other of said last-mentioned two photosensors and said numerical display means for actuating the latter to display a "5" as the least significant digit of the three digit number when said other photosensor is activated.

6. In a pressure gauge system comprising a pressure gauge having:
a gauge body with a gas pressure inlet;
a rotary shaft in said gauge body;
and pressure responsive means in said gauge body for rotating said shaft proportional to the gas pressure at said inlet; the improvement which comprises:
an encoder disc fastened to the shaft and extending substantially perpendicular thereto, said disc carrying a plurality of discrete light transmitting elements at different positions radially and circumferentially of the disc;
a lamp operatively arranged to shine light through at least one of said light transmitting elements on the disc;
a stator plate fixedly mounted inside said gauge body in parallel confronting relationship to said disc;
a plurality of photosensors mounted on said stator plate for selective registration individually with corresponding light transmitting elements on the disc in different rotational positions of the disc;
numerical display means for displaying a three digit decimal number;
and circuit means operatively connected between said photosensors and said numerical display means for converting the optically sensed rotational position of the shaft into the two most significant digits of the three digit number;

said photosensors on the stator plate including an outer row of ten photosensors at the same radial distance from the shaft and evenly spaced in close succession circumferentially;

said light transmitting elements on the disc include three elements at said same radial distance from the shaft which are spaced apart circumferentially by ten times the spacing between successive ones of said ten photosensors;

said circuit means includes means connected between said ten photosensors and said numerical display means for actuating the latter to display as the second most significant digit of the three digit number ten successive digits from "1" to "0" in successive rotational positions of the shaft in the forward direction as any of said three light transmitting elements registers in succession individually with the ten photosensors;

said light transmitting elements on the disc also include a single element at a shorter radial distance from the shaft than said three light transmitting elements;

said photosensors include an inner row of first, second, third and fourth photosensors in succession circumferentially at said shorter radial distance from the shaft, said first and second photosensors in said inner row being spaced circumferentially from each other by less than the angle between successive photosensors in said outer row, said second and third photosensors in said inner row being spaced circumferentially from each other by substantially the same angular distance as the spacing between the first and tenth photosensors in said outer row, and said third and fourth photosensors in said inner row being spaced circumferentially from each other by less than the angle between successive photosensors in said outer row;

said circuit means includes means connected between said first photosensor of said inner row and said numerical display means to actuate the latter
  (a) to display the digit "9" as said second most significant digit of the three digit number, and
  (b) to prevent the display of the digit "1" as the most significant digit of the three digit number
when said single light transmitting element on the disc registers with said first photosensor of said inner row;

said circuit means includes means connected between said second photosensor of said inner row and said numerical display means to actuate the latter to display the digit "1" as the most significant digit of said three digit number when said single light transmitting element on the disc registers with said second photosensor of said inner row and to maintain said display of the digit "1" as the most significant digit until said single light transmitting element registers with the fourth photosensor in said inner row, during the forward rotation of the shaft;

said circuit means includes means connected between said third photosensor of said inner row and said numerical display means to actuate the latter
  (a) to display the digit "1" as the most significant digit of said three digit number, and
  (b) to prevent the display of the digit "2" as the most significant digit of said three digit number, and
  (c) to display the digit "9" as the second most significant digit of said three digit number
when said single light transmitting element on the disc registers with said third photosensor of said inner row;

and said circuit means includes means connected between said fourth photosensor of said inner row and said numerical display means to actuate the latter
  (a) to display the digit "2" as the most significant digit of said three digit number, and
  (b) to prevent the display of the digit "1" as the most significant digit of said three digit number
after said single light transmitting element on the disc registers with said fourth photosensor of said inner row during the forward rotation of the shaft.

7. A system according to claim 6, wherein:

said numerical display means includes means for displaying a "0" or a "5" as the least significant digit of the three digit number;

said light transmitting elements on the disc include two circular rows of fifteen elements each at different radial distances from the shaft;

said photosensors on the stator plate include two photosensors positioned respectively at said last-mentioned radial distances from the shaft for registration alternately with the successive light transmitting elements in said last mentioned two circular rows as the shaft rotates in the forward direction;

and said circuit means includes means connected between one of said last-mentioned two photosensors and said numerical display means for actuating the latter to display a "0" as the least significant digit of said three digit number when said one photosensor is activated, and means connected between the other of said last-mentioned two photosensors and said numerical display means for actuating the latter to display a "5" as the least significant digit of the three digit number when said other photosensor is activated.

8. A pressure gauge system according to claim 6, wherein said light transmitting elements are fiber optic lenses at said different positions on the disc, and further comprising a reflector operatively associated with said lamp to substantially concentrate the light from the lamp on a small area of the disc to illuminate just the lens or lenses which appear in said small area in different rotational positions of the disc.

9. A pressure gauge system according to claim 6, wherein said light transmitting elements are separate fiber optic arms extending individually from said lamp to said different positions on the disc.

* * * * *